United States Patent
Bauer et al.

(10) Patent No.: US 10,074,196 B2
(45) Date of Patent: Sep. 11, 2018

(54) RECONSTRUCTING A THREE-DIMENSIONAL IMAGE DATASET FROM TWO-DIMENSIONAL PROJECTION IMAGES, X-RAY DEVICE AND COMPUTER PROGRAM

(71) Applicants: Sebastian Bauer, Erlangen (DE); Andreas Maier, Erlangen (DE); Yan Xia, Erlangen (DE)

(72) Inventors: Sebastian Bauer, Erlangen (DE); Andreas Maier, Erlangen (DE); Yan Xia, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 80 days.

(21) Appl. No.: 15/356,587

(22) Filed: Nov. 19, 2016

(65) Prior Publication Data
US 2017/0148192 A1    May 25, 2017

(30) Foreign Application Priority Data
Nov. 19, 2015    (DE) .................. 10 2015 222 837

(51) Int. Cl.
*G06K 9/00*    (2006.01)
*G06T 11/00*    (2006.01)
*G06T 7/00*    (2017.01)

(52) U.S. Cl.
CPC .......... *G06T 11/003* (2013.01); *G06T 7/0012* (2013.01); *G06T 7/0081* (2013.01); *G06T 2207/10116* (2013.01)

(58) Field of Classification Search
CPC .......................................... G06T 2207/10116
See application file for complete search history.

(56) References Cited

U.S. PATENT DOCUMENTS

2011/0052030 A1*  3/2011  Bruder ............... A61B 6/032
                                            382/131
2013/0004045 A1*  1/2013  Dennerlein ........ A61B 6/032
                                            382/131
(Continued)

OTHER PUBLICATIONS

Dennerlein Frank, et.al.: "Approximate truncation robust computed tomography—ATRACT", in: Phys. Med. Biol., vol. 58, pp. 6133-6148, 2013.
(Continued)

*Primary Examiner* — Oneal R Mistry
(74) *Attorney, Agent, or Firm* — Lempia Summerfield Katz LLC (57) ABSTRACT

A method for reconstructing a three-dimensional image dataset from two-dimensional projection images includes recording the projection images using a collimator downstream of an X-ray source. A local Laplace filter is initially applied to the projection data of the projection images during the reconstruction using filtered back-projection. After this, high-frequency spikes arising in the Laplace-filtered projection data at boundaries to the image region are removed by a spike filter, and a global residual filter is applied. A fit parameter describing a fit function approximating the projection data characteristic in the uncorrected projection images inside the image region is determined based on at least marginal values of the projection data present at the boundaries. Next, following on from the use of the residual filter, an additive correction of the residual-filtered projection data in the image region is performed with the fit function scaled by a scaling factor.

15 Claims, 4 Drawing Sheets

(56) References Cited

U.S. PATENT DOCUMENTS

2013/0259342 A1* 10/2013 Bruder ................. G06T 11/006
　　　　　　　　　　　　　　　　　　　　　　　382/131
2014/0050295 A1*  2/2014 Dennerlein ............ A61B 6/032
　　　　　　　　　　　　　　　　　　　　　　　378/4

OTHER PUBLICATIONS

Feldkamp L.A. et al., "Practical cone-beam algorithm", in: Journal of the Optical Society of Americal A, vol. 1, No. 6, 1984, pp. 612-619.
Hsieh J., et.al. : "A novel reconstruction algorithm to extend the CT scan field-of-view" Med. Phys. Nr. 31, vol. 9, pp. 2385-2391, Sep. 2004.
Xia, Y.: "Towards Clinical Application of a Laplace Operator-based Region of Interest Reconstruction Algorithm in C-arm CT", Copyright (c) 2010 IEEE.

\* cited by examiner

FIG 1
(Stand der Technik)

RECONSTRUCTING A THREE-DIMENSIONAL IMAGE DATASET FROM TWO-DIMENSIONAL PROJECTION IMAGES, X-RAY DEVICE AND COMPUTER PROGRAM

This application claims the benefit of DE 10 2015 222 837.1, filed on Nov. 19, 2015, which is hereby incorporated by reference in its entirety.

BACKGROUND

The present embodiments relate to reconstructing a three-dimensional image dataset from two-dimensional projection images.

In the field of X-ray imaging, it is known to reconstruct higher-dimensional image datasets from lower dimensional projection images, where, for example, three-dimensional image datasets may be reconstructed from two-dimensional projection images. In conventional computed tomography, at least one X-ray source is rotated about the patient in a gantry for this purpose in order to record one-dimensional or two-dimensional projection images. It has, however, already been proposed for the concept also to be transferred to other X-ray devices (e.g., X-ray devices having a C-arm). In each case, the computed tomography uses ionizing radiation as the X-ray technology. The reduction of the quantity of ionizing radiation used for a CT scanner is advantageous both for the patient and for any personnel present (e.g., if the computed tomography is being deployed as part of a medical intervention, (to monitor the progress of an intervention)).

Hence, the use of collimators (e.g., diaphragms) that enable the field of view actually illuminated by X-ray radiation to be restricted to a volume of interest (VOI) inside the patient has also been proposed for computed tomography. The collimator thus reduces the X-ray dose significantly by using collimation to block (or at least severely attenuate) X-ray radiation in regions outside a predetermined volume of interest. This type of computed tomography is frequently referred to as VOI CT.

One problem with VOI CT is that the associated projection images are generally subjected to data truncation, which provides that, for example, parallel to the plane in which the scanning trajectory lies, the object to be scanned (e.g., the patient) is at least in part not fully mapped in the projection images. The consequence of this is that conventional image reconstruction algorithms no longer produce satisfactory results, since in the case of truncated projection images in which the image region, which is illuminated despite the collimator, shows the object truncated, the object is fully fluoroscoped in projection images oriented differently for this purpose. The information is thus inconsistent, since part of the attenuated region is not represented in the truncated projection images.

To resolve this problem, the proposal has been made, for example, in an article by F. Dennerlein and A. Maier, "Approximate truncation robust computed tomography—ATRACT", Physics in Medicine and Biology, Vol. 58, p. 6133-6148, 2013, for the so-called ATRACT algorithm, which forms a suitable approach for the reconstruction of a volume of interest from truncated projection data (cf. the article by Y. Xia et al., "Towards Clinical Application of a Laplace Operator-based Region of Interest Reconstruction Algorithm in C-arm CT", IEEE Transactions on Medical Imaging, Vol. 33, p. 593-606, 2014). Even with strong lateral data truncation the ATRACT algorithm may effectively reduce truncation artifacts and thus provides high-quality reconstructions without an explicit extrapolation or previous knowledge being required. Thus the ATRACT algorithm is suitable for clinical use. As the cited article by Y. Xia et al. shows, in comparison to techniques based on extrapolation (cf. J. Hsieh et al., "A novel reconstruction algorithm to extend the CT scan field-of-view", Medical Physics, Vol. 31, No. 9, p. 2385-2391, 2004), significantly better results are achieved with the ATRACT algorithm.

The ATRACT algorithm is based on splitting the conventional ramp filter inside the well-known frame of the filtered back-projection (cf. the FDK algorithm in L. A. Feldkamp et al., "Practical cone-beam algorithm", J. Opt. Soc. Am., Vol. 1, No. 6, p. 612-619, 1984) in a local and a nonlocal partial filter. As part of the local partial step of the filter step, a Laplace filter (e.g., a second derivation) is implemented by applying a Laplace operator. In the nonlocal substep of the filter step, a radon-based residual filtering is performed (cf. steps A and B in section 3.3. of the article by F. Dennerlein and A. Maier cited by reference herein). As an alternative to a radon-based residual filtering, a convolution is also possible. It is important that in the ATRACT algorithm the high-frequency spikes that occur at the truncation boundaries (e.g., the boundaries of the image region) after the Laplace filtering are removed. This removal of the high-frequency spikes takes place ultimately prior to the nonlocal residual filtering, consequently by a spike filter, but may, however, be integrated into the residual filter, in that an inner integration of the radon-based or convolution residual filter is restricted to the interior of the image region (cf. the formula (20) in the cited article by F. Dennerlein and A. Maier). This removal of the spikes provides that the ATRACT algorithm is robust in respect of the truncation, and prevents the well-known cupping/capping artifacts if the normal FDK algorithm is deployed with truncated image data.

Hitherto, most ATRACT examinations related to the reconstruction of volumes of interest (VOI) that are essentially located in the center of the object to be scanned ("centered case") are provided. In experimental examinations, however, it has been found that during the reconstruction of volumes of interest that are not located in the center of the object ("noncentered case"), artifacts may arise if the ATRACT algorithm is applied. This may also occur if an intensity gradient occurs elsewhere in a plane parallel to the plane of the scanning trajectory.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a possibility of reducing artifacts in the case of noncentered volumes of interest and/or intensity gradients during reconstruction with the ATRACT algorithm is provided.

In a method, in a first correction step, a fit parameter describing a fit function approximating the projection data characteristic in the uncorrected projection images inside the image region is determined based on at least marginal values of the projection data present at the boundaries. In a second correction step following on from the use of the residual filter, an additive correction of the residual-filtered projection data in the image region is performed with the function scaled by a scaling factor.

After the second correction step, the additively corrected projection data may then be used for back-projection, as is essentially known, in order to obtain the image dataset. Thanks to the use of the collimator, the result is thus, for example, a truncation of the scanned object (e.g., a patient), which is relevant to the reconstruction, since only one volume of interest is to be scanned in the object, which ultimately is mapped in the image region on the X-ray detector. The truncation consequently lies, for example, parallel to a plane in which the scanning trajectory of the X-ray source lies during the recording of the projection images. In other words, the truncation exists, for example, laterally in lines of the X-ray detector that run parallel to the acquisition plane in which the scanning trajectory lies.

In the case of one or more of the present embodiments, the ATRACT method described in the cited article by F. Dennerlein and A. Meier, in which instead of using a ramp filter in the filter step a local Laplace filter is initially applied to the projection data of the projection images in two substeps, after which high-frequency spikes arising in the Laplace-filtered projection data at boundaries of the image region are removed by the spike filter and a global residual filter is applied, is again employed. The spike filter may be integrated into the residual filter, as described by the formula (20) in the referenced article by F. Dennerlein and A. Maier. Consequently, the filter step further includes, as essentially known in the prior art, at least two substeps (e.g., a local substep and a nonlocal (global) substep).

In one embodiment, the ATRACT algorithm is supplemented with correction steps that return information to the reconstruction that was essentially lost because of the modified filtering. This is because in the context of one or more of the present embodiments it has been known that the reason for artifacts arising, for example, in noncentered cases is that a gradient of the image values is present between the boundaries of the image region (e.g., parallel to a plane of the scanning trajectory), which is evident in various amplitudes of the high-frequency spikes at the left and right truncation boundary. However, since these high-frequency spikes are removed, information is lost. This provides that the removal of the high-frequency spikes may have a significant influence on the global intensity gradients in the ATRACT-filtered projections when compared to ramp-filtered, non-truncated projection data. The back-projection propagates this gradient artifact from the projection domain into the volume domain, so that in the reconstructed three-dimensional image dataset that shows the volume of interest, global intensity gradients may occur as artifacts. Intensity gradients in noncentered cases occur, for example, because as a result of the shape of most objects to be scanned (e.g., patients) that may be approximated by an elliptical shape, different radiation paths through the object are present in different regions of the projection images, which increase, for example, directions.

In one or more of the present embodiments, this intensity gradient artifact is removed or at least reduced by proposing an extension of the ATRACT algorithm, in which the information lost by the removal of the peaks in the ATRACT-filtered projection images is added again at least in part in order to compensate for the intensity gradient artifact. An easy-to-implement, additive correction that depends on the projection data characteristic in the uncorrected projection images inside the image region (e.g., which emulates this) is sufficient to obtain very high quality image datasets largely or wholly free of intensity gradient artifacts.

In the processing of the projection images, it is known for any collimator shadows present at the boundary of the image region, effects that do not allow the projection data outside the image region to fall immediately to zero to be cropped, which may also advantageously happen in the context of one or more of the present embodiments (e.g., if the structure of the peaks existing at the boundary is taken into consideration in the context of the correction). Since both the position of the image region from the scanning geometry and the collimator settings as well as the normal collimator shadow behavior are known, a corresponding cropping of projection data outside the image region may be provided before the Laplace filter is applied.

An easy-to-implement but nevertheless effective embodiment emerges when the fit function describes a linear characteristic of the projection data of the image region of interest between the boundaries and the gradient of the fit function is determined as a fit parameter. Despite an extremely simple model for the intensity gradients being applied in the projection image, which consequently is geared to differences in the magnitude between the two boundaries, excellent results are achieved in terms of the reduction of artifacts. The linear gradient between the left and right edge of the image region is consequently determined as a fit parameter $$m_1 = (h_l - h_r)/w, \quad (1)$$

where w represents the width of the image region in each projection image and h designates the marginal values. The projection data characteristics are considered individually for each projection image, in the direction of the truncation relevant to the reconstruction (e.g., therefore parallel to the plane in which the scanning trajectory lies) since the correction steps are of course also project-image-related. More complex approaches to the description of the projection data characteristic may also be provided (e.g., higher-order fit functions), but no further significant improvement has been shown in examinations, so that the simple linear model is already sufficient.

The marginal values may be determined as an average value, formed across all lines of the projection images, of the outermost values of the projection data and/or of the peak amplitudes at the boundary in the Laplace-filtered projection images. Since two-dimensional projection images are considered, a particular number of lines are present in the truncation direction relevant to the reconstruction (e.g., parallel to the plane of the scanning trajectory (a circuit)), so that particularly reliable marginal values may then be formed if an average is taken of the outermost values of the individual lines or the peak amplitudes at the boundary in the Laplace-filtered projection images. The amplitudes of the peaks, as are present in the Laplace-filtered projection image not yet freed of the peaks, may be used as a measure for the edge amplitudes of the projection data. Since, as was stated in the introduction, cropping is possible in any case at the edge of the image region, so that there is no longer a collimator shadow, the second derivation is a direct measure of the "transition" of the projection image data that occurs there and may be used as a surrogate for the outermost values of the projection data at the boundary. Since in any case a scaled addition of the respective values of the fit function to the residual-filtered projection data takes place, any scaling that occurs is not important.

If a linear model is assumed, the following occurs from the gradient $m_1$ as a fit parameter as a correction measure in the second correction step.

$$p_{corr,1}(u,v) = p_{ATRACT}(u,v) + m_2 u, \quad (2)$$

where $P_{ATRACT}$ describes the fully ATRACT-filtered projection data and $m_2$ is the gradient of the linear model which is associated with the gradient $m_1$ via a scaling factor c:

$m_2=cm_1$. The variables u and v are the indices of the projection image pixels in the line and column direction.

Generally, the scaling factor is expediently determined empirically by measurement and/or simulation (e.g., by a comparison of corrected test projection data determined by the additive correction with ramp-filtered, untruncated test projection data). The scaling factor may therefore be determined empirically (e.g., by comparing) for a test set of test projection images. The test projection data corrected in accordance with formula (2) with ramp-filtered, untruncated test projection data of the same test set ("ground truth").

A development emerges if the additive correction is performed only for projection images, in which the marginal values vary at least by a predefined limit value or the gradient determined as a fit parameter exceeds the limit value. For example, it may be provided that the additive correction is performed only for the part of the projection images for which, for example, the condition $m_1 > \tau$ applies, where $\tau$ describes a predefined limit value, which has, for example, been determined empirically. Therefore, if the difference between the projection data on the left and the right side of the projection image or the peak amplitudes at the boundaries are somewhat small (e.g., $m_1 < \tau$ applies), the additive correction is not used (e.g., in that $m_2$ is set to zero for this case). In such projection images, it may thus be assumed that very little information is lost too, so that it is more advantageous to leave the projection data untouched. This results in a further improvement in image quality. As already mentioned, the limit value may be determined empirically by measurements and/or simulations.

A development of the method emerges if in the second correction step one of the marginal values and/or a correction value describing an average value of the projection data in the image region scaled with a correction factor is likewise added to the residual-filtered projection data as an offset correction. A further problem of the original ATRACT algorithm is that the average intensity level of the projection data is likewise lost by the removal of the peaks at the truncation boundaries after application of the Laplace operator (cf. also the integration contained in the residual filter) in order ultimately to attain the effect of a ramp filter again. In this way, bias-like intensity artifacts may occur in the volume domain of the image dataset. The result of these would be that user-side visualization presets (e.g., desired accentuations that emerge from a particular value range of intensity values of the three-dimensional image dataset) no longer supply the desired result (e.g., an accentuation of the soft tissues). To compensate for this bias-like artifact, a common basis for all projection images is created by selecting one of the marginal values or a correction value describing an average value of the projection data in the image region as the correction value, multiplying the one marginal value by an identical correction factor for all projection images, and adding the multiplied one marginal value to the residual-filtered projection data in order to recreate the lost, average intensity level in the projection image. Thus, for example, provision may be made for selecting the greater value from $h_l$ and $h_r$, multiplying, for example, by an empirically selected, predefined correction factor k, and adding the result to the residual-filtered projection data:

$$p_{corr,2}'(u,v) = p_{ATRACT}'(u,v) + k \cdot \max(h_l, h_r) \quad (3)$$

The correction factor, designated k in the example, may be determined depending on a scanned anatomical region and/or empirically. For example, the correction factor is determined such that intensity value ranges are obtained in the volume domain (e.g., in the three-dimensional dataset) in the way that the intensity value ranges also occur in reconstructions from non-truncated projection data. Thus, problems with visualization settings are avoided. By orientation to the intensity level in the original projection image, which, as explained above, may in turn also be described by the spike amplitudes, a comparable adjustment is made for all projection images.

The combination of the two proposed extensions, and consequently the two additions in the second correction step, may be written in the example as the correction formula $$p_{corr}(u,v) = p_{ATRACT}(u,v) + m_2 u + k \cdot \max(h_l, h_r) \quad (4)$$

This corresponds to a combination of formulas (2) and (3).

Overall, the advantage of the described approach for extending the ATRACT algorithm is that residual artifacts of the existing ATRACT algorithm are compensated for, where, in one embodiment, a correction is achieved both for gradient-type and for bias-type intensity artifacts. The amplitudes of the high-frequency spikes on the left and right truncation boundaries of the image region, which are simply cropped after the Laplace filtering and not considered further in traditional ATRACT algorithms, may be taken into account in this process. This enables a significantly better image quality to be achieved (e.g., for non-centered cases). The success of the method is confirmed by experiments relating to phantom and clinical projection data.

As well as the method, one or more of the present embodiments also relate to an X-ray device having an X-ray source with an associated collimator and a control device designed for performing the method. All embodiments relating to the method may be transferred by analogy to the X-ray device, with which the advantages already mentioned may also consequently be achieved. For example, the control device consequently also has at least one correction unit in addition to a filter unit for the usual ATRACT filtering. The correction unit is then able to perform the first and the second correction step of the method. A back-projection unit uses the then additively corrected projection data for the back-projection and for obtaining the image dataset.

One or more of the present embodiments also relate to a computer program that performs the act of the method when the program is executed on a computing device. Also for this purpose, the embodiments continue to apply to the method and to the X-ray device. The computing device may consequently correspond to the control device of the X-ray device. The computer program may be stored on an electronically readable data medium, which may, for example, be a non-transient data medium (e.g., a CD-ROM). If the data medium is read by a computing device, the described computer program may be executed accordingly.

The X-ray device may otherwise be a normal computed tomography device, in which the X-ray source is guided, for example, in a gantry. However, the X-ray device may be configured as a C-arm X-ray device, in which the X-ray source and an X-ray detector are arranged opposite one another on a C-arm.

DETAILED DESCRIPTION

Figure 1:
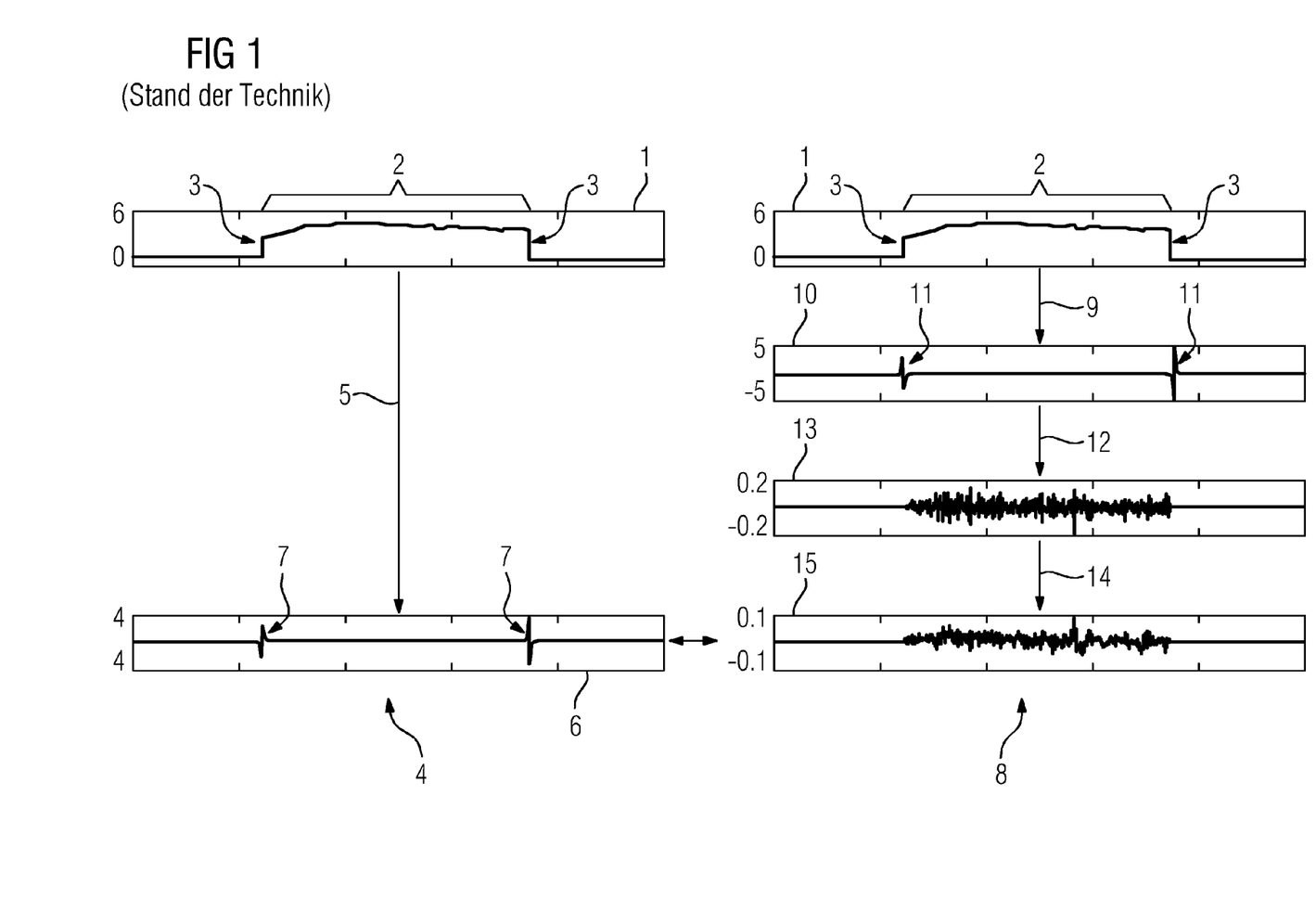
FIG. 1 shows a comparison of the procedures and effects in the FDK algorithm and in the ATRACT algorithm according to the prior art.

FIG. 1 shows how projection data changes with filtering in algorithms of filtered back-projection of the prior art. Graph 1 shows projection data characteristic at both ends in a line of a projection image before a filter step is performed in the context of the filtered back-projection. FIG. 1 shows that a collimator was used to limit a field of view of a scanning arrangement used to a volume of interest (VOI) in the object, which is then mapped onto an image region 2. There is consequently a truncation in a direction relevant to the reconstruction. The value of the projection data is zero outside the image region 2. For example, this is explicitly set to crop collimator shadows and other effects arising as a result of the geometry of the collimator. There is consequently a sharply sloping edge at boundaries 3 of the image region 2.

In the reconstruction with the FDK algorithm illustrated on the left side 4, a ramp filter is used in the filter step according to arrow 5. This has the result that overshoots 7 occur at the boundaries 3 (e.g., appearing in the image as image artifacts). The result graph 6 shows the projection data characteristic in the line after the ramp filtering, To improve the image quality of reconstructions in the recording of truncated projection images, the ATRACT algorithm illustrated in the right-hand part 8, in which a modified filter step is applied using different partial filters, was proposed.

In a first substep (e.g., arrow 9) of the filter step, a Laplace filter is applied. Consequently, a two-dimensional Laplace operator, which is effective locally, is applied to the projection data. This results in a characteristic, as shown in graph 10, in which high-frequency spikes 11 arise at the boundaries 3. The high-frequency spikes 11 are then removed by using a spike filter (e.g., arrow 12), so that a projection data characteristic, as shown in graph 13, is produced (e.g., also the amended size scale for this purpose). The spike filter may be integrated into the formula of a residual filter. The application of the residual filter after the removal of the spikes 11 is symbolized by the arrow 14. An overall filtered projection data characteristic, freed from overshoots 7, is finally obtained (e.g., graph 15 for the characteristic of the residual-filtered projection data).

However, when the spikes 11 are cut away, information is also removed from the projection data (e.g., about an intensity gradient inside the image region 2, as is clearly present in FIG. 1, and the information about the intensity level in the projection data). The extended form of the ATRACT algorithm to be presented below reintroduces at least part of this information in a simple way to the filtered projection data, and consequently starts, for example, in a correction step in the filtered projection data in graph 15.

Figure 2:
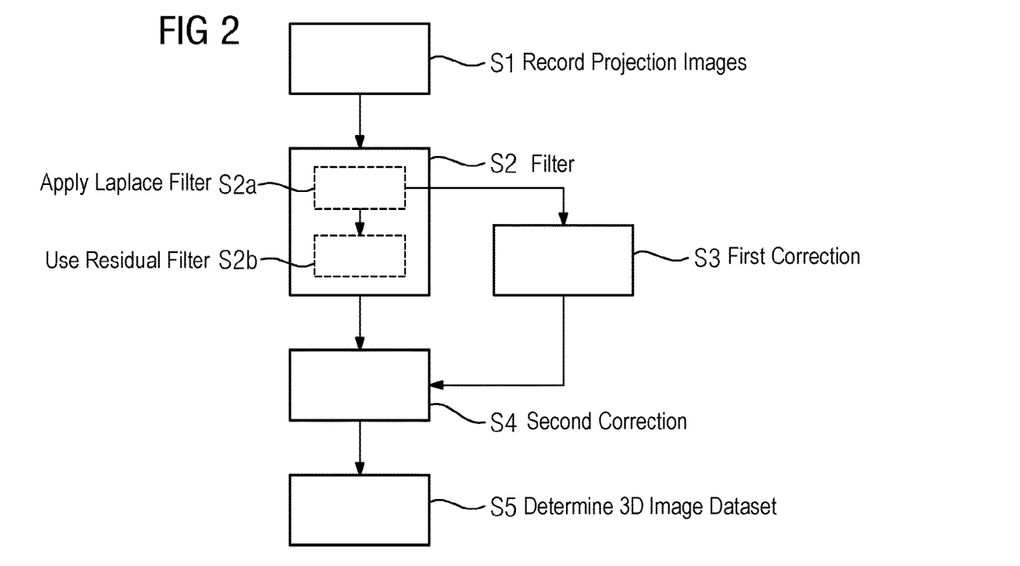
FIG. 2 shows a flowchart of one embodiment of a method.

FIG. 2 shows an exemplary embodiment of a method for reconstructing a three-dimensional image dataset from two-dimensional projection images. The method truncates the object to be scanned (e.g., a patient) in at least one direction parallel to the plane of the scanning trajectory of the X-ray source during the recording of the projection images, and consequently does not completely show the object to be scanned, as was also the case in the projection data characteristic in graph 1. The basis for the reconstruction algorithm described here is further represented by the ATRACT algorithm, so that the filtering takes place according to the ATRACT algorithm in a filter act S2 after the recording of the projection images in act S1 and any cropping of collimator shadows as was explained with reference to FIG. 1 in this regard. Consequently, in a first subact S2a of the act S2, as described, the Laplace filter is applied to the projection data of the projection images. In a second subact S2b, the residual filter, which integrally contains the spike filter, is used, as generally known, to obtain the residual-filtered projection data and thus the filtered projection data overall.

The exemplary embodiment illustrated here starts after the subact S2a with a first correction S3, by initially determining the left and right spike amplitudes of the spikes 11 (cf. FIG. 1) for all lines of a projection image. An average value is then formed as the marginal value over all lines of a projection image on both boundaries 3 (e.g., left and right). According to the formula (1), a gradient is then determined as a fit parameter between the marginal values in a linear model.

Figure 3:
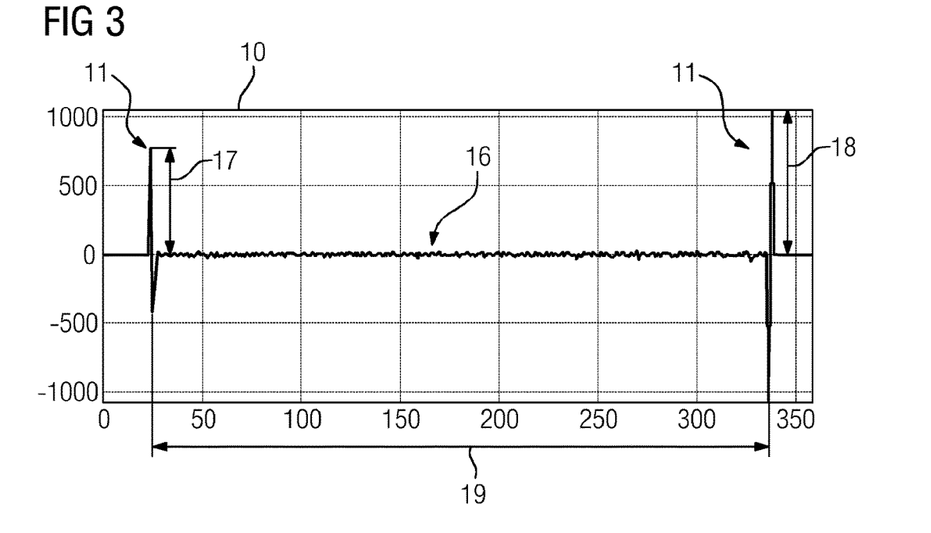
FIG. 3 shows a line profile of a projection line after an application of the Laplace filter.

The spike amplitudes may be used, since these map the level of the transition edge at the boundary 3 (cf. also graphs 1 and 10 of FIG. 1). The high-frequency spike on the left has a smaller amplitude than the high-frequency spike 11 on the right, as is also to be expected from the projection data characteristic in FIG. 1. To allow a more detailed explanation, FIG. 3 shows graph 10 on a larger scale. FIG. 3 shows the Laplace-filtered projection data characteristic 16, in which the high-frequency spikes 11 are shown. Also shown, by double-ended arrows, are the spike amplitude 17 of the left spike 11 ($h_l$ in formula (1)) and the spike amplitude 18 of the right spike 11 ($h_r$ in formula (1)) and the width 19 of the image region 2 (w in formula (1)).

The spike amplitudes 17, 18 are of different sizes, and consequently, at least with regard to the illustrated lines, a difference in intensity exists between the right and the left boundary 3. If this is essentially continued through all lines, an intensity gradient in the image region 2 may be inferred overall. The gradient of this in a linear model is quickly produced via the formula (1). Cases may also occur in which gradients with different characteristics are found in individual lines. Here, however, only the average, significant effect over all lines is considered.

The projection data may also be worked along the corresponding lines with external values as an alternative to the spike amplitudes 17, 18. Even more complex approaches than a linear model may be used, which may then use the unfiltered projection data characteristic (Graph 1) as the basis, but have been found to be not absolutely necessary in examinations.

In addition to the determined gradient $m_1$ the maximum of the spike amplitudes 17, 18 (e.g., max ($h_l$, $h_r$)) is stored in the first correction S3. This calculation of gradients and dimensions is performed individually for the intensity level for each of the projection images.

After the completion of the filter act S2, the information obtained in the first correction S3 is then used in a second correction S4 for correcting the filtered projection data of the individual projection images. First, a check is made for each projection image to establish whether the determined gradient $m_1$ falls below a predefined limit value that has been determined empirically. If this is the case, the value $m_2=0$ is set. Otherwise, the value $m_2$ results as the product of the gradient $m_1$ with a scaling factor c. The scaling factor c is the same for all projection images and has been determined empirically by measurements and/or simulation such that, in test sets of test projection images recorded without truncation and thus artificially truncatable, the test projection data produced after the second correction S4 corresponds to ramp-filtered, untruncated test projection data of the test set. A correction factor k is predefined for scaling the correction value max ($h_l$, $h_r$) for all projection images equally depending in this case on the anatomical region.

Figure 4:
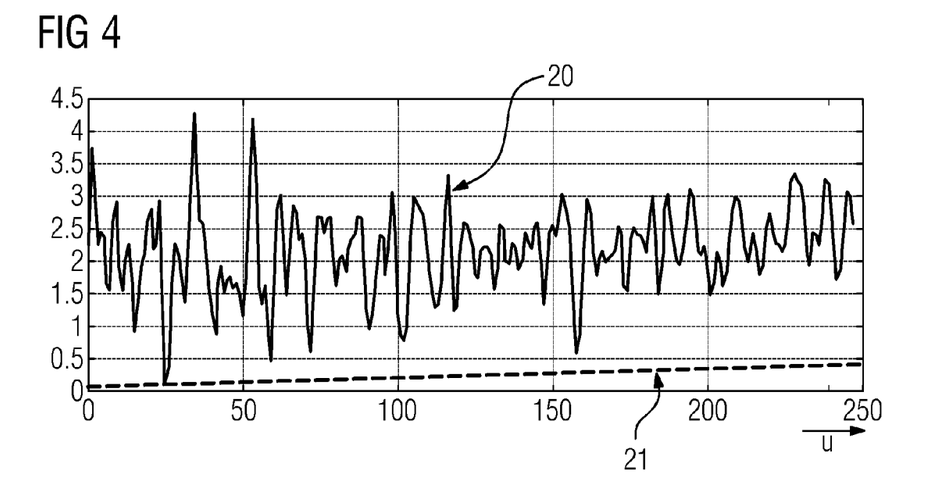
FIG. 4 shows a line profile of a residual-filtered projection line and a first correction portion.

The additive correction of the filtered projection data is performed according to the formula (4). By way of explanation, reference is made to FIG. 4, which shows an as yet uncorrected filtered projection data characteristic 20 in the image region 2 (detail corresponding to Graph 15 from FIG. 1) together with the linear correction portion 21, given by $m_2 u$. The values of the scaled fit function thus produced, correction portion 21, are added pixel-by-pixel to the values of the projection data characteristic 20. What is not shown in greater detail here is the constant additive correction for restoring the information relating to the intensity level.

The three-dimensional image dataset is determined by back-projection, as this is known in principle, in act S5 (cf. FIG. 2 again).

Figure 5:
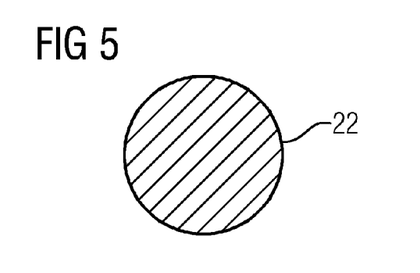
FIG. 5 shows a section through a reconstruction of a phantom from untruncated projection images with the FDK algorithm.
Figure 6:
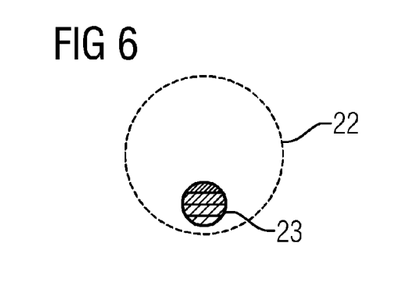
FIG. 6 shows a section through a reconstruction of a volume of interest at the edge of the phantom when the traditional ATRACT algorithm is used.
Figure 7:
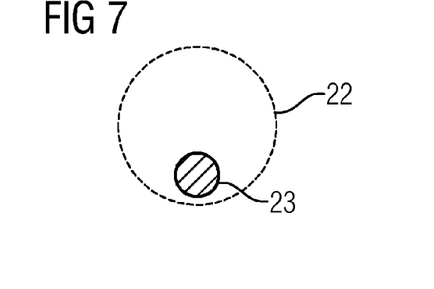
FIG. 7 shows the section from FIG. 6 when the extended ATRACT algorithm is used.

FIGS. 5 to 7 show the effect of the method of one or more of the present embodiments in schematic section images of a cylindrical phantom. FIG. 5 relates to a reconstruction of the entire (e.g., unstructured) phantom 22. The phantom 22, as indicated by the hatching, may weaken uniformly and also appears with a homogeneous grayscale value.

The cases shown in FIGS. 6 and 7 now relate to the reconstruction of a volume of interest 23, which is evidently not located centrally in the phantom 22, but rather toward the edge, so that consequently, this is a non-centered case. Truncated projection images of the volume of interest 23 are recorded using a collimator—. In the case of FIG. 6, the reconstruction is performed with the usual ATRACT algorithm, and in FIG. 7, with the illustrated exemplary embodiment of the method. As indicated by the different hatching in FIG. 6, an intensity gradient arises in the section image illustrated (e.g., in the three-dimensional image dataset), which originates from the loss of information caused by the removal of the spikes 11.

This intensity gradient artifact may no longer be seen in the illustration shown in FIG. 7. The reintroduction of the information carried out by the scaled addition of the fit function in the second correction S4 results in a homogeneous gray coloring. The correction factor k has been selected here such that the same intensity is present in the reconstruction as is present in untruncated scan and FDK reconstruction (cf. FIG. 5).

Figure 8:
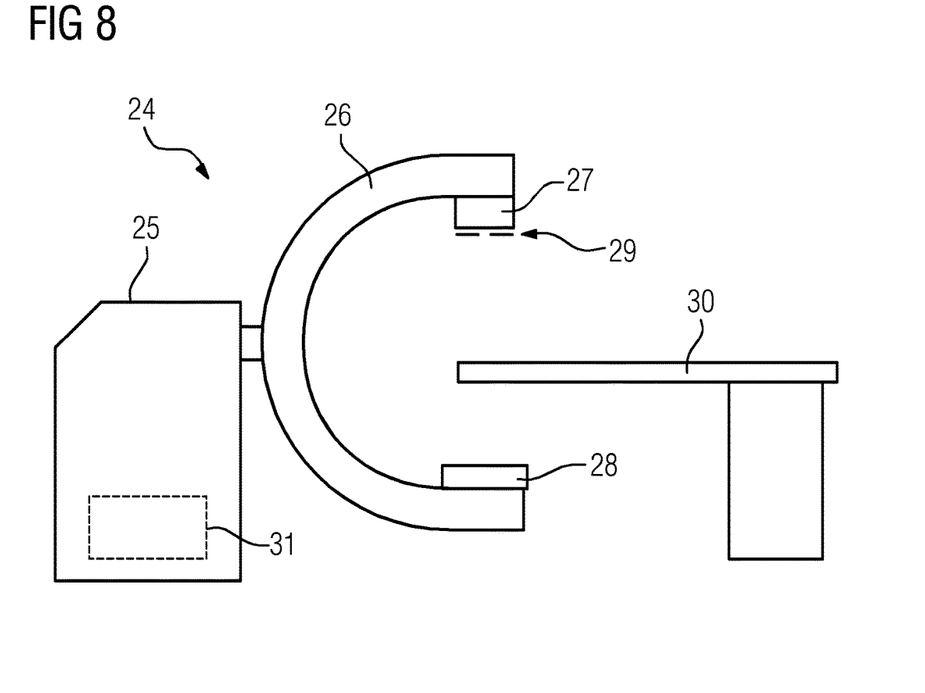
FIG. 8 shows one embodiment of an X-ray device.

FIG. 8 shows a schematic diagram of one embodiment of an X-ray device 24. The X-ray device 24 is, for example, configured as a C-arm-X-ray device. The C-arm X-ray device 24 consequently includes, mounted on a stand 25, a C-arm 26 in which an X-ray source 27 and an X-ray detector 28 (e.g., a flat-panel detector) are arranged opposite one another. A collimator 29 (e.g., a diaphragm) is provided (e.g., associated with the X-ray source 27 and integrated into the X-ray source 27). The collimator 29 allows the X-ray radiation to be limited to a volume of interest 23. The maneuverability of the C-arm 26 enables the scanning arrangement formed from the X-ray detector 28 with the X-ray source 27 to be moved around a patient situated on a patient couch 30 according to a scanning trajectory in order to record the projection images accordingly.

The operation of the X-ray device 24 is controlled by a control device 31, which is also configured to perform the method, as has been described with reference to FIG. 3.

Although the invention has been illustrated and described in greater detail by the exemplary embodiments, the invention is not limited by the examples disclosed. The person skilled in the art will be able to derive other variations on this basis without moving beyond the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for reconstructing a three-dimensional (3D) image dataset from two-dimensional (2D) projection images recorded from different projection directions, the method comprising:

recording the 2D projection images using a collimator downstream of an X-ray source used for a scan, to restrict unattenuated X-ray radiation to an image region of interest;

initially applying a local Laplace filter to projection data of the 2D projection images during the reconstruction using filtered back-projection;

removing, by a spike filter and a global residual filter, high-frequency spikes arising in the Laplace-filtered projection data at boundaries to the image region of interest, which expands the Laplace filter to a ramp filter;

determining, in a first correction step, a fit parameter describing a fit function approximating a projection data characteristic in uncorrected projection images inside the image region of interest based on at least marginal values of the projection data present at the boundaries; and performing, in a second correction step, following on from the use of the global residual filter, an additive correction of the residual-filtered projection data in the image region of interest with the fit function scaled by a scaling factor.

2. The method of claim 1, wherein the global residual filter integrally contains the spike filter.

3. The method of claim 1, wherein the fit function describes a linear characteristic of the projection data of the image region of interest between the boundaries and a gradient of the fit function is determined as the fit parameter.

4. The method of claim 1, wherein the marginal values are determined as an average value, formed across all lines of the projection images, of outermost values of the projection data, of spike amplitudes at the boundary in the Laplace-filtered projection images, or of the outermost values of the projection data and the spike amplitudes at the boundary in the Laplace-filtered projection images.

5. The method of claim 1, wherein the scaling factor is determined empirically by measurement, simulation, or measurement and simulation.

6. The method of claim 5, wherein the simulation comprises a comparison of corrected test projection data determined by the additive correction with ramp-filtered, untruncated test projection data.

7. The method of claim 1, wherein the additive correction is performed only for projection images, in which the marginal values vary at least by a predefined limit value or the gradient determined as a fit parameter exceeds the predefined limit value.

8. The method of claim 5, wherein the predefined limit value is determined empirically by measurements, simulations, or measurements and simulations.

9. The method of claim 1, wherein in the second correction step, one of the marginal values, a correction value describing an average value of the projection data in the image region of interest, or a combination thereof is scaled with a correction factor as well as added to the residual-filtered projection data as an offset correction.

10. The method of claim 9, wherein the correction factor is predefined depending on a scanned anatomical region, is determined empirically, or is predefined depending on the scanned anatomical region and is determined empirically.

11. An X-ray device comprising:
    an X-ray source comprising an associated collimator; and
    a control device configured to reconstruct a three-dimensional (3D) image dataset from two-dimensional (2D) projection images recorded from different projection directions, the reconstruction comprising:
        recordation of the 2D projection images using the collimator downstream of the X-ray source, to restrict unattenuated X-ray radiation to an image region of interest;
        initial application of a local Laplace filter to projection data of the 2D projection images during the reconstruction using filtered back-projection;
        removal, by a spike filter and a global residual filter, of high-frequency spikes arising in the Laplace-filtered projection data at boundaries to the image region of interest, which expands the Laplace filter to a ramp filter;
        determination, in a first correction step, of a fit parameter describing a fit function approximating a projection data characteristic in uncorrected projection images inside the image region of interest based on at least marginal values of the projection data present at the boundaries; and
        performance, in a second correction step, following on from the use of the global residual filter, of an additive correction of the residual-filtered projection data in the image region of interest with the fit function scaled by a scaling factor.

12. In a non-transitory computer-readable storage medium storing instructions executable by a computing device for reconstructing a three-dimensional (3D) image dataset from two-dimensional (2D) projection images recorded from different projection directions, the instructions comprising:
    recording the 2D projection images using a collimator downstream of an X-ray source used for a scan, to restrict unattenuated X-ray radiation to an image region of interest;
    initially applying a local Laplace filter to projection data of the 2D projection images during the reconstruction using filtered back-projection;
    removing, by a spike filter and a global residual filter, high-frequency spikes arising in the Laplace-filtered projection data at boundaries to the image region of interest, which expands the Laplace filter to a ramp filter;
    determining, in a first correction step, a fit parameter describing a fit function approximating a projection data characteristic in uncorrected projection images inside the image region of interest based on at least marginal values of the projection data present at the boundaries; and
    performing, in a second correction step, following on from the use of the global residual filter, an additive correction of the residual-filtered projection data in the image region of interest with the fit function scaled by a scaling factor.

13. The non-transitory computer-readable storage medium of claim 12, wherein the global residual filter integrally contains the spike filter.

14. The non-transitory computer-readable storage medium of claim 13, wherein the fit function describes a linear characteristic of the projection data of the image region of interest between the boundaries and a gradient of the fit function is determined as the fit parameter.

15. The non-transitory computer-readable storage medium of claim 13, wherein the marginal values are determined as an average value, formed across all lines of the projection images, of outermost values of the projection data, of spike amplitudes at the boundary in the Laplace-filtered projection images, or of the outermost values of the projection data and the spike amplitudes at the boundary in the Laplace-filtered projection images.

\* \* \* \* \*